US00PP22814P2

(12) United States Plant Patent
Warren

(10) Patent No.: US PP22,814 P2
(45) Date of Patent: Jun. 26, 2012

(54) EUROPEAN HORNBEAM TREE NAMED 'JFS-KW1CB'

(50) Latin Name: *Carpinus betulus*
Varietal Denomination: JFS-KW1CB

(75) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 296 days.

(21) Appl. No.: 12/799,002

(22) Filed: Apr. 14, 2010

(51) Int. Cl.
*A01H 5/00* (2006.01)

(52) U.S. Cl. ..... Plt./216

(58) Field of Classification Search ..... Plt./216
See application file for complete search history.

(56) References Cited

OTHER PUBLICATIONS

Anonymous. "'Emerald Avenue' Hornbeam JFS Introductions" available at http://www.jfschmidt.com/introductions/emeraldavenue/index.html accessed Sep. 30, 2011.*

Anonymous. "'Emerald Avenue' Hornbeam" J. Frank Schmidt & Son Co. Accessed Sep. 30, 2011.*

* cited by examiner

*Primary Examiner* — Wendy C Haas

(74) *Attorney, Agent, or Firm* — Klarquist Sparkman, LLP

(57) ABSTRACT

A variety of *Carpinus betulus* which combines a unique combination of faster growth, with an upright growth habit with a sturdy trunk, and upward orientated branches, and darker green, larger summer leaves.

10 Drawing Sheets

Latin name of the genus and species of the plant claimed: *Carpinus betulus*.

Variety denomination: 'JFS-KW1CB'.

BACKGROUND OF THE INVENTION

During 1995 and 1996, I obtained a large number of seedlings of a number of *Carpinus* species, as I was interested in the potential for development of improved cultivars within this genus for street and landscape use. In 1999, I recognized that one particular seedling of *Carpinus betulus* that had been planted in a cultivated area in a nursery row in 1996 was unique. In particular, I noticed that it was unusually vigorous, had a strong, upright growth habit, possessed unusually large and dark green leaves, and developed very nice yellow fall color.

I closely observed this tree over the next few years. In 2002, 2003, and 2004, I directed the asexual propagation of my new tree by grafting in Boring, Oreg., onto *Carpinus betulus* seedling understock. From each of these propagations, I obtained a small number of trees that I planted out in plots in nursery rows for further observation and testing.

From these propagated plants, I became convinced that the features of my new tree were firmly fixed in successive generations and that my new tree possesses unique characteristics making it particularly suitable for use as a street tree.

BRIEF SUMMARY OF THE INVENTION

My new cultivar possesses a unique combination of characteristics in that it combines an upright growth habit with a sturdy trunk and uniformly upward orientated branches, faster growth than typical of the species, and darker green, larger summer leaves.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
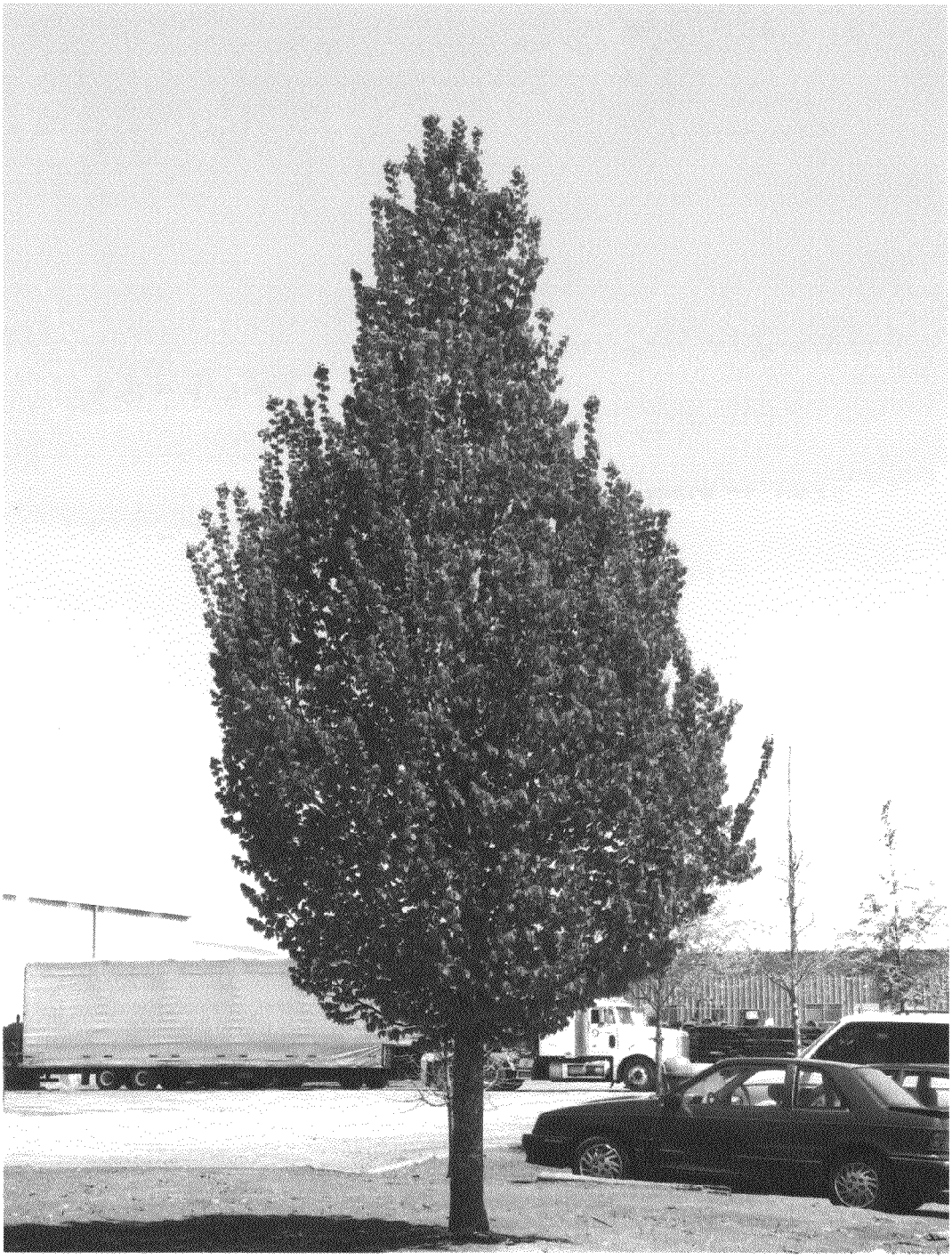
FIG. 1: Shows the original tree in its dark green summer foliage and the upright nature of its growth habit.
Figure 2:
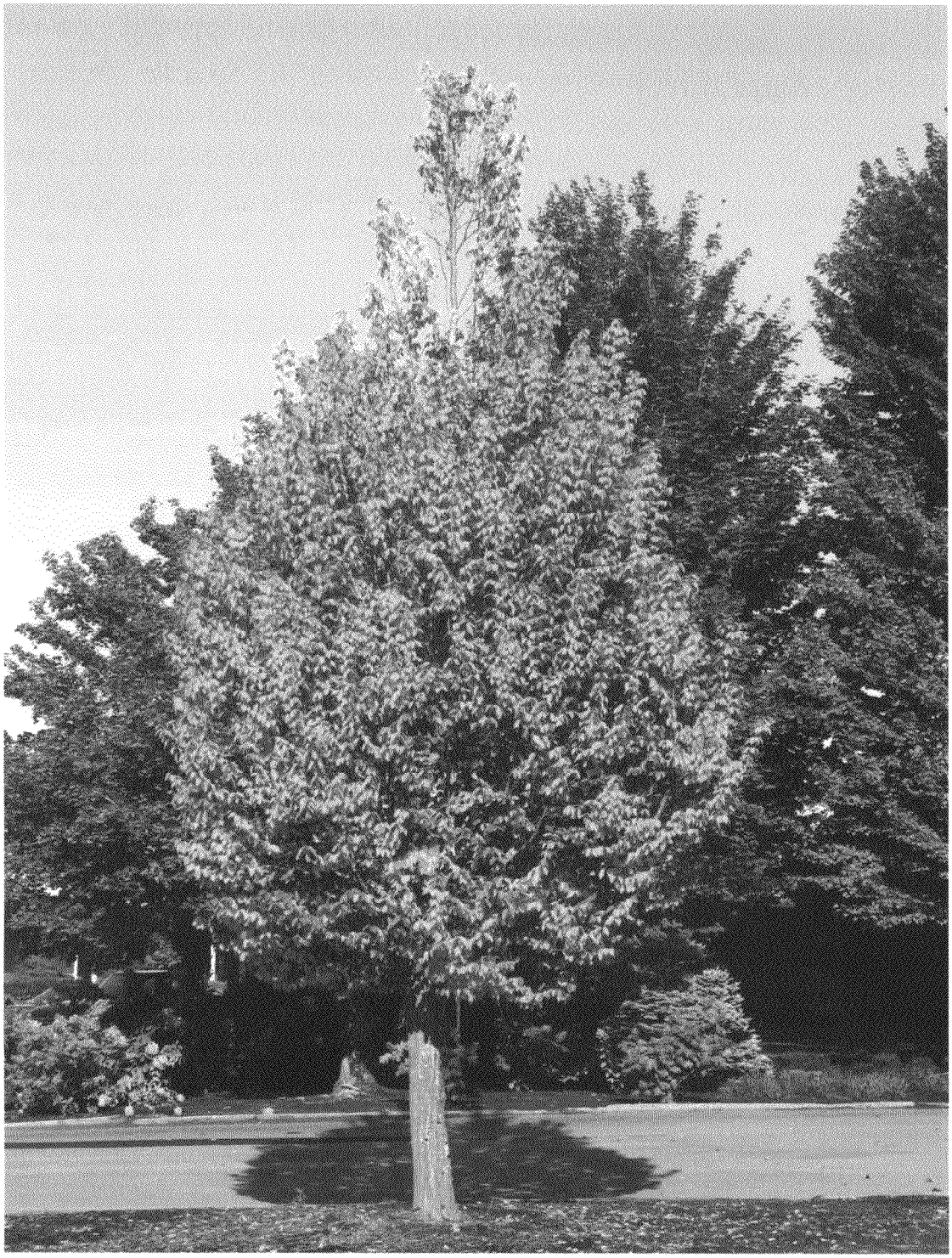
FIG. 2: Shows the original tree in its yellow fall color and illustrates the broadly pyramidal to ovate form.
Figure 3:
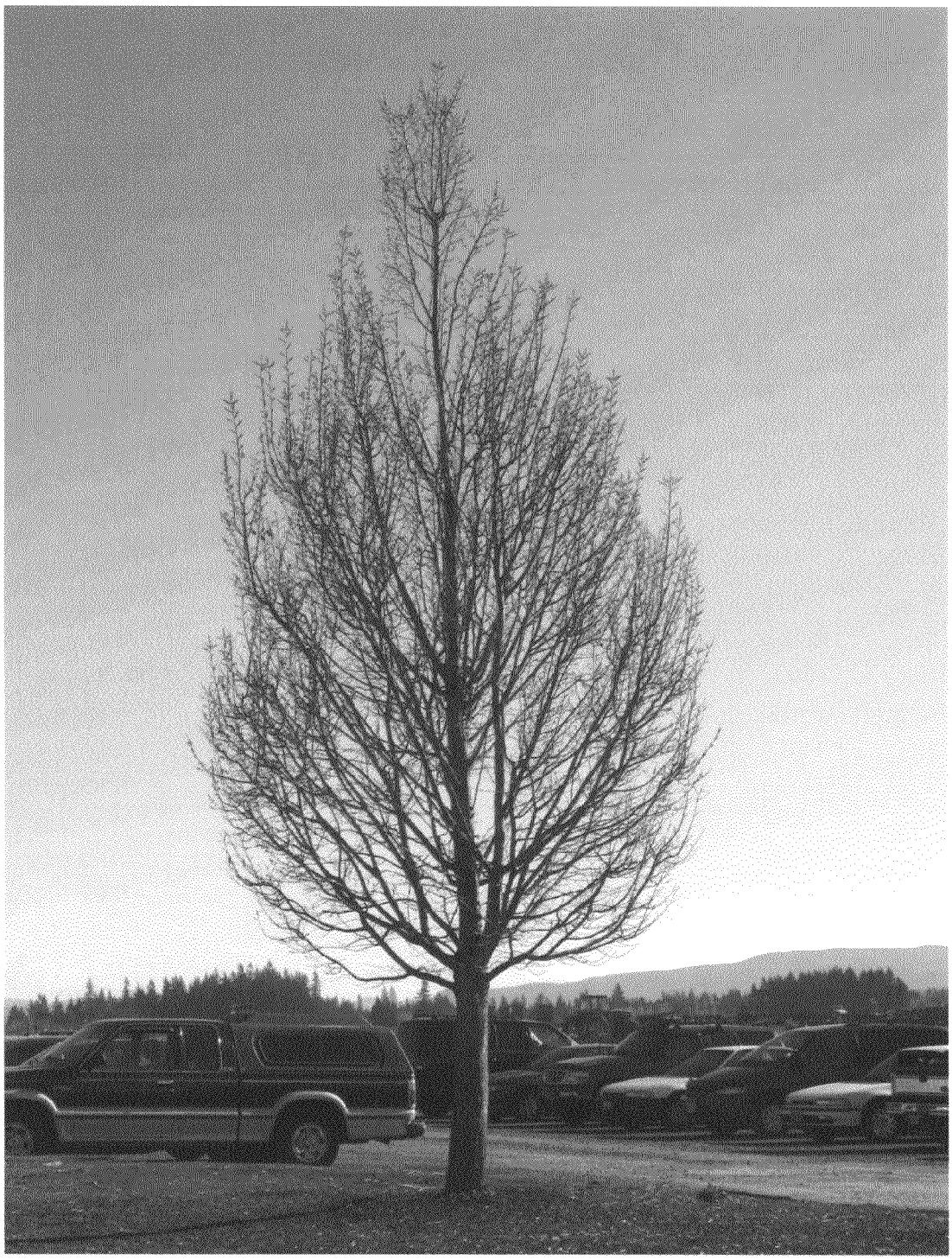
FIG. 3: Shows the original tree dormant in winter and illustrates the sturdy, upright trunk, the upward curving branch structure and overall growth form.
Figure 4:
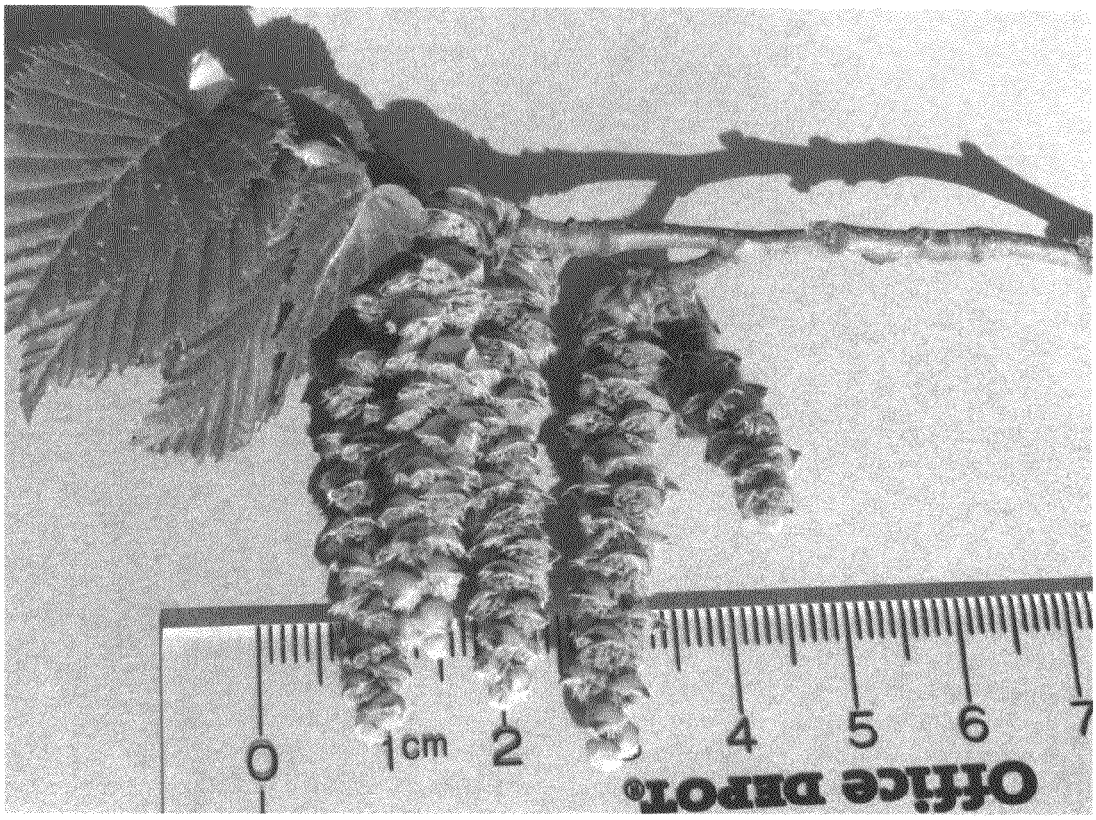
FIG. 4: Shows the male catkins in full flower.
Figure 5:
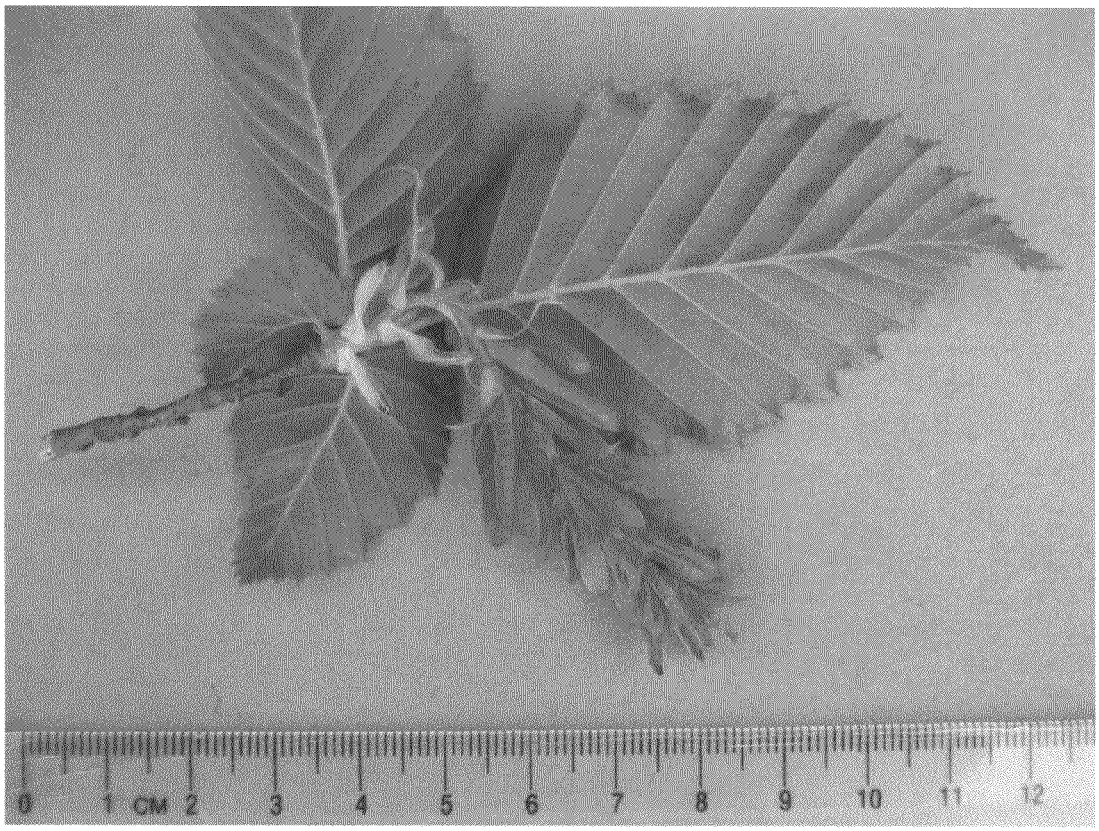
FIG. 5: Shows a female flower catkin a few days after pollination.
Figure 6:
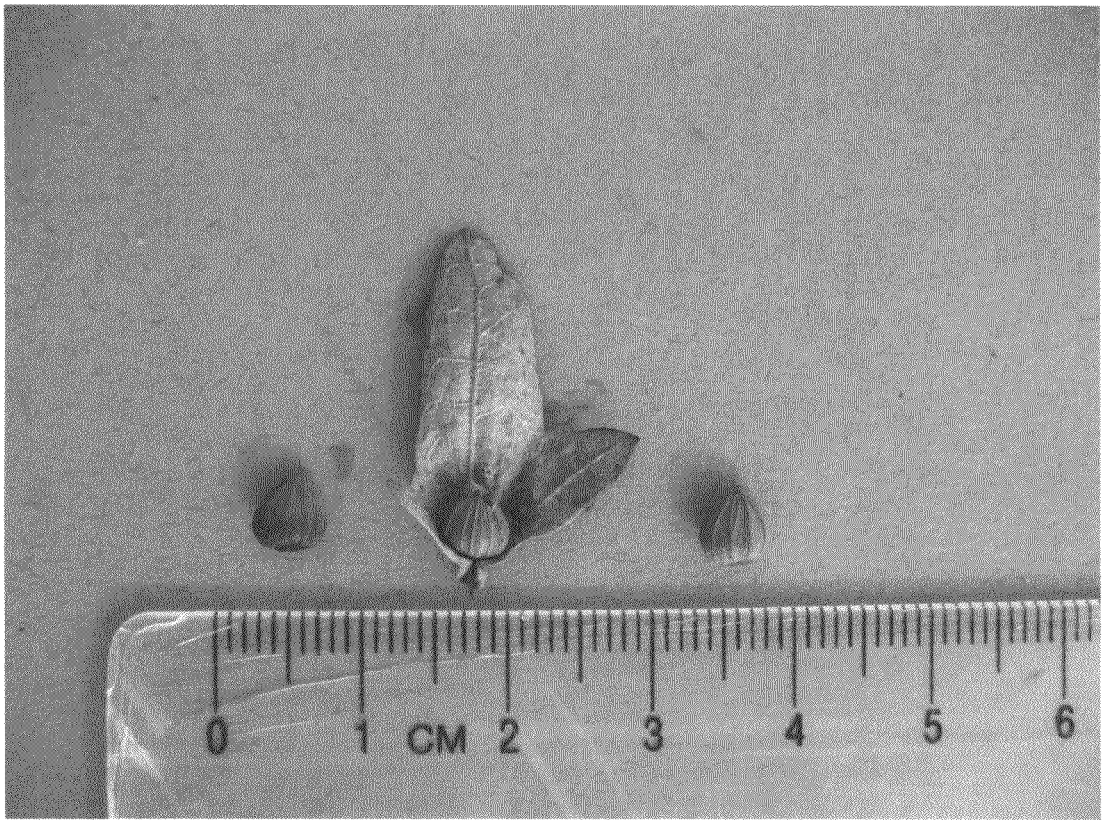
FIG. 6: Shows three mature nutlets, the center one enclosed in a trident shaped bract.
Figure 7:
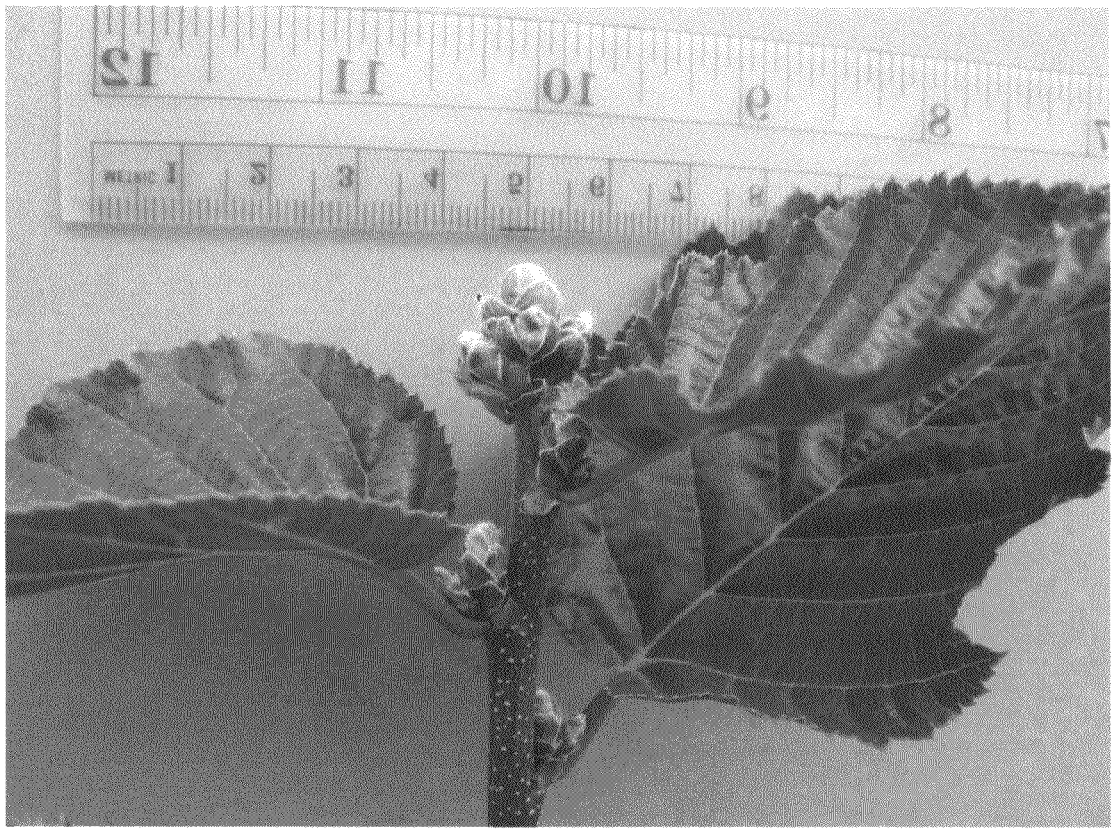
FIG. 7: Shows the terminal section of a twig at the end of summer and illustrates the large buds with broadly acute to bluntly rounded apices and the thickness of the twig near the terminal end.
Figure 8:
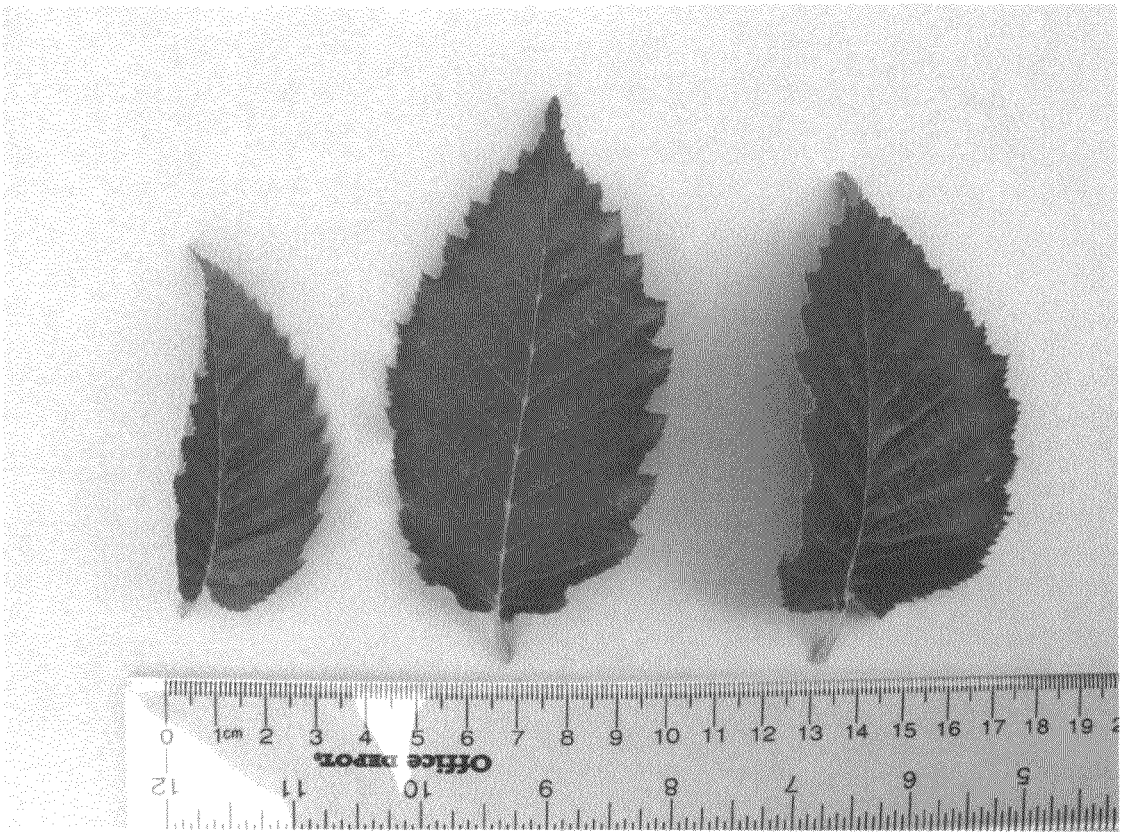
FIG. 8: Shows the summer leaf with its broadly ovate shape, dark green color, doubly serrate margin, and tendency to curl slightly downward along the central vein.
Figure 9:
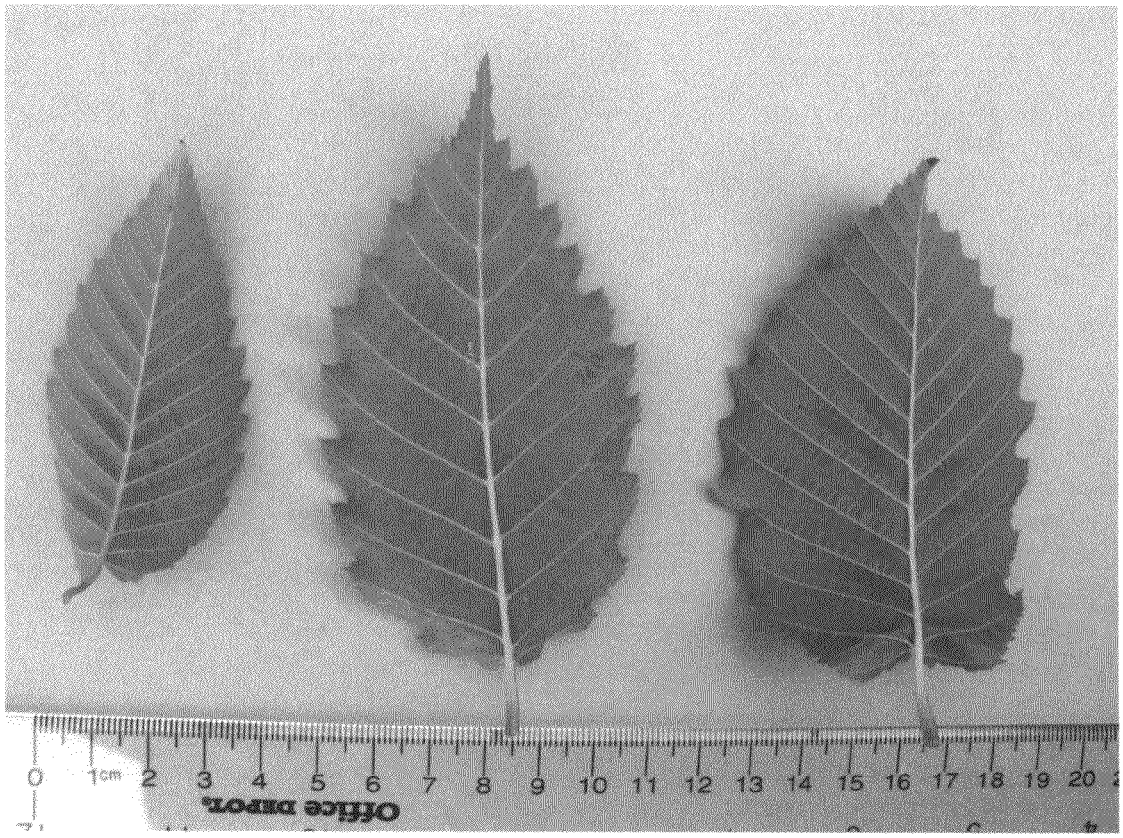
FIG. 9: Shows the underside of the summer leaf illustrating the prominent parallel veins.
Figure 10:
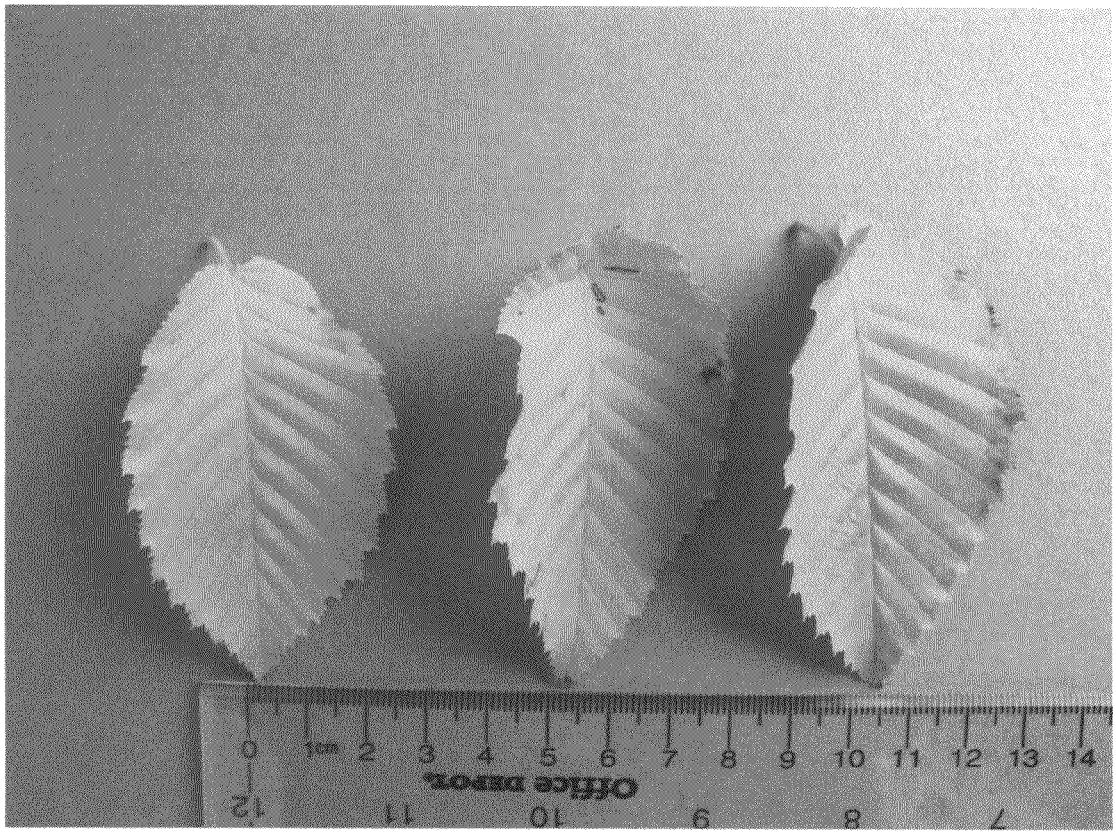
FIG. 10: Shows leaves at peak fall color, illustrating coloration, the broadly ovate shape, the parallel veins, and the doubly serrate margin.

The following detailed description of the 'JFS-KW1CB' variety is based on observations of the original tree and two, three, and four year old progeny. The observed progeny were trees which were growing under nursery conditions in Boring, Oreg.

The following is a detailed description of my new hornbeam tree with color descriptions using terminology in accordance with The Royal Horticultural Society (London) Colour Chart© 1986, except where ordinary dictionary significance of color is indicated.

Scientific name: *Carpinus betulus* 'JFS-KW1CB'.

Parentage:

*Seed parent.*—*Carpinus betulus.*

*Pollen parent.*—*Carpinus betulus.*

Tree:

*Overall shape.*—Broadly pyramidal to ovate.

*Height.*—8.7 meters at 14 years of age.

*Width.*—4.1 meters at 14 years of age.

*Caliper.*—27.3 cm at 10 cm; 21.2 cm at 1 meter, at 14 years of age.

*Trunk.*—Sturdy, strong, straight.

*Trunk bark texture.*—Smooth.

*Trunk bark color.*—Mature bark color: Mostly Greyed-Green 197A to 197B, with a few smaller areas colored similarly to Greyed-Green 195A.

*Primary branches.*—Sturdy, rather symmetrically arranged, branching regularly, curving upward in orientation.

*Branch color.*—Similar to Grey-Brown 199A.

*Branch lenticels.*—Small, 1 mm, rounded to slightly oval, generally disappearing into the bark by the fourth year, Greyed-Green 196A.

*Dormant buds.*—Imbricate, large, fat, 7-10 mm long× 4-6 mm thick, broadly acute to bluntly rounded tip.

*Internodes.*—3 cm to 5 cm on young nursery grown trees; 2 cm on mature tree.

*Hardiness.*—Has tolerated temperatures to 10 degrees F. without damage in Boring, Oreg. It has not been tested at lower temperatures, but it is believed to have Zone 5 cold hardiness similar to the species.

*Disease resistance.*—Similar to the species.

Leaves: Except as otherwise noted, observations are from twenty vigorous growth leaves.

*Arrangement.*—Alternate.

*Overall shape.*—Broadly ovate with a slight tendency to curl downward along the central vein. Secondary veins radiating from the central vein are generally parallel.

*Margin.*—Doubly serrate.

*Tip.*—Acute to short acuminate, often twisted up to 90° in relationship to plane of leaf.

*Base.*—Cordate.

*Texture.*—Upper surface has a raised and folded appearance between veins making surface look corrugated when young. Veins impressed above; prominent below. Leaf upper surface becomes smoother as the tree ages.

*Sheen.*—Slightly glossy when leaves are young, becoming dull (upper surface) as leaves mature.

*Length.*—7.0 cm to 11.5 cm.

*Width.*—5.0 cm to 8.0 cm wide.

*Petioles.*—8 mm to 20 mm long×1 mm to 2 mm in diameter. Yellow-green 152B to Yellow-green 153A with a tint of Red 46B on the sun side.

*Stipules.*—In pairs surrounding buds, papery thin, sometimes early deciduous. Yellow-Green 148C on first appearance, becoming Yellow-Green 153B to Yellow-Green 153D, finally drying to Greyed-Orange 177A and usually dropping.

*Spring leaf color, first emerging leaves.*—Green 143A with slight blush of Greyed-Purple 183A at margins.

*Summer leaf color.*—Upper leaf surface: Green 139A. Lower leaf surface: Green 137B to Green 138A. Vein: Yellow-Green 145B.

*Fall leaf color.*—Yellow-Orange 22A to Orange 24B on upper surface; Yellow-Orange 22B to 22C on lower surface.

*Pubescence.*—Glabrous except for a few sparse hairs along the veins on the underside of the leaf.

*Persistence.*—Tree is deciduous.

Flowers:

*Overall.*—Monoecious, with male and female catkins. Flowers open with expanding leaves in spring.

*Male catkin.*—Cylindrical 25 mm to 35 mm long, about 7 mm in diameter at the upper end tapering to about 3 mm in diameter at tip. Yellow-Green 145D, each flower reduced to numerous stamens clustered close together, subtended by a bract, bract margins pilose.

*Female catkins.*—Flowers in 25 mm to 40 mm long chains, each flower surrounded by a trident shaped, glabrous, three lobed bract. Bracts and flowers are Yellow-Green 145B. Individual female flowers are inconspicuous, hidden within bract, with only two linear stigmas protruding, each 2 mm to 3 mm long.

*Pollen.*—Yellow 11B.

*Fragrance.*—None.

*Flowering date.*—In Boring, Oreg., average: First bloom: March 28. Peak bloom: April 14. End of bloom: April 25.

Fruit: Ripens in fall, typically by November 1 in Boring, Oreg. Observations are from a sampling of typical fruit.

*Type.*—A nutlet born at the base of a papery 3 lobed, trident shaped bract.

*Size.*—2 to 4 mm.

*Shape.*—Slightly ovoid to slightly deltoid.

*Surface.*—Hard, longitudinally finely ribbed.

*Color.*—Greyed-Orange 165C when first mature, darkening with age to Greyed-Orange 177B.

*Bracts.*—2.5 cm to 3.0 cm×1.5 cm to 2.0 cm, 3 lobed, trident shaped, glabrous, Greyed-Orange 165C darkening to Greyed-Orange 177C as seed matures.

*Seeds.*—One per nutlet. Ovoid, 1 mm×1.5 mm, Greyed-Orange 165A.

*Fruit production.*—Light.

Comparison to the species and other cultivars:

The species, *Carpinus betulus*, forms a broadly oval to rounded canopy with branches that spread rather widely. In the nursery, typical young seedling trees of the species are moderate in growth rate with somewhat weak stems and horizontal to sprawling branches with moderate sized buds. My new variety, 'JFS-KW1CB' differs in that it matures to a broadly pyramidal to ovate form with strong, upright curving branches. In addition, my new variety has more narrow branch angles and a thicker trunk and thicker twigs in the nursery and possesses larger, more rounded buds.

The two most similar existing cultivars are 'Fastigiata' (unpatented) and 'Frans Fontaine' (unpatented). These two cultivars differ significantly in that they have smaller, more pointed buds, more slender twigs, and smaller, narrower, and lighter green leaves.

The following two tables define the most significant differences.

TABLE 1

Comparison to the species

| Feature | 'JFS-KW1CB' | *Carpinus betulus* seedling |
|---|---|---|
| Growth rate: | Moderately fast, 145 cm in two years | Moderate, 127 cm I two years |
| Branches: Branch angle, 3 year trees: | Strongly upright, sturdy 30-45 degrees at crotch; averages 20 degrees when measured 30 cm branch distance from crotch | Weakly horizontal to sprawling 60-120 degrees at crotch; averages 90 degrees when measured 30 cm branch distance from crotch |
| Leaf shape: | Broadly ovate | Ovate |
| Leaf size: | 7-11.5 cm long × 5-8 cm wide | 6-8 cm long × 3-5 cm wide |
| Leaf color, summer, upper surface: | Darker green, Green 139A | Lighter, more yellow-green, Yellow-Green 147A |
| Young twig diameter: | Large, 3-5 mm, measured 2 cm from end | Moderate, 1-2 mm, measured 2 cm from end |
| Young trunk caliper: | Sturdy, 17.8 mm diameter at 3 years of age, measured 10 cm from ground | Moderate, 13.5 mm diameter at 3 years of age, measured 10 cm from ground |
| Dormant buds: | 7-10 mm long × 4-6 mm diameter, broadly acute to bluntly rounded tip | 5-6 mm long × 2-3 mm diameter, acute tip |

TABLE 2

Comparison to other cultivated varieties

| Feature | 'JFS-KW1CB' | 'Fastigiata' | 'Frans Fontaine' |
|---|---|---|---|
| Leaf shape: | Broadly ovate | Ovate | Ovate |
| Leaf size: | 7-11.5 cm long × 5-8 cm wide | 5-8 cm long × 3.5-5 cm wide | 6-9 cm long × 4-5 cm wide |
| Leaf color, summer, upper surface: | Darker green, Green 139A | Lighter, more yellow-green, Yellow-Green 147A | Lighter, more yellow-green, Yellow-Green 147A |
| Young twig diameter: | Large, 3-5 mm, measured 2 cm from end | Moderate, 1-2 mm, measured 2 cm from end | Moderate, 1-2 mm, measured 2 cm from end |
| Dormant buds: | 7-10 mm long × 4-6 mm diameter, broadly acute to bluntly rounded tip | 7-9 mm long × 3 mm diameter, sharply acute tip | 5-7 mm long × 3 mm diameter, acute tip |

I claim:

1. A new and distinct variety of European Hornbeam tree, substantially as herein shown and described.

* * * * *